United States Patent

Khosravi et al.

[11] Patent Number: 5,824,054
[45] Date of Patent: Oct. 20, 1998

[54] COILED SHEET GRAFT STENT AND METHODS OF MAKING AND USE

[75] Inventors: Farhad Khosravi, San Mateo; Michael Hogendijk, Palo Alto; John Spiridigliozzi, Belmont; Michael R. Ross, Hillsborough, all of Calif.

[73] Assignee: Endotex Interventional Systems, Inc., Menlo Park, Calif.

[21] Appl. No.: 820,213

[22] Filed: Mar. 18, 1997

[51] Int. Cl.⁶ ............................................ A61F 2/06
[52] U.S. Cl. ............................ 623/1; 606/191; 606/198; 606/194; 623/12
[58] Field of Search .................... 623/1, 12; 606/191, 606/194, 198

[56] References Cited

U.S. PATENT DOCUMENTS

| | | | |
|---|---|---|---|
| 4,577,631 | 3/1986 | Kreamer | 128/334 R |
| 4,665,918 | 5/1987 | Garza et al. | 128/343 |
| 5,078,726 | 1/1992 | Kreamer | 606/194 |
| 5,100,429 | 3/1992 | Sinofsky et al. | 606/195 |
| 5,211,658 | 5/1993 | Clouse | 623/1 |
| 5,219,355 | 6/1993 | Parodi et al. | 606/191 |
| 5,266,073 | 11/1993 | Wall | 623/12 |
| 5,275,622 | 1/1994 | Lazarus et al. | 623/1 |
| 5,330,500 | 7/1994 | Song | 606/198 |
| 5,366,473 | 11/1994 | Winston et al. | 606/198 |
| 5,423,885 | 6/1995 | Williams | 623/1 |
| 5,441,515 | 8/1995 | Khosravi et al. | 606/194 |
| 5,443,500 | 8/1995 | Sigwart | 623/1 |
| 5,456,713 | 10/1995 | Chuter | 623/1 |
| 5,571,173 | 11/1996 | Parodi | 623/1 |
| 5,578,075 | 11/1996 | Dayton | 623/12 |
| 5,649,977 | 7/1997 | Campbell | 606/194 |
| 5,700,285 | 12/1997 | Myers et al. | 623/12 |
| 5,700,286 | 12/1997 | Tartaglia et al. | 604/104 |
| 5,707,385 | 1/1998 | Williams | 604/104 |

*Primary Examiner*—Paul B. Prebilic
*Attorney, Agent, or Firm*—Fish & Neave; Nicola A. Pisano

[57] ABSTRACT

A prosthesis is provided for treatment of aneurysms, occlusive disease of vessels and body organs, and arterio-venous fistulas, comprising an expandable coiled sheet portion having a biocompatible graft affixed thereto. The graft material, preferably a polytetrafluoroethylene ("PTFE") or polyesther material, is affixed to the coiled sheet portion by sintering, suturing, or bonding using a biocompatible adhesive. The coiled sheet portion comprises a lattice formed from a biocompatible material, and may include one or more rows of locking teeth adjacent one edge of the coiled sheet that interengage openings in an opposing edge of the coiled sheet portion to retain the prosthesis at a desired expanded diameter. The prosthesis has a small delivery profile, making it suitable for use in a variety of body vessels. Methods of making and deploying the prosthesis are also provided.

67 Claims, 7 Drawing Sheets

COILED SHEET GRAFT STENT AND METHODS OF MAKING AND USE

FIELD OF THE INVENTION

The present invention relates to prostheses for treatment of aneurysms, arterio-venous fistulas, obstructive vascular disease and other applications. More specifically, the present invention relates to prostheses including coiled sheet portions having a biocompatible material affixed thereto which may be used in a variety of applications as an internal bandage.

BACKGROUND OF THE INVENTION

Millions of people worldwide are afflicted each year with vascular diseases, ranging from vascular obstructive disease, such as artheriosclerosis, to diseases that weakened the arteries or other vessels, resulting in potentially fatal aneurysms and arterio-venous fistulas. Arterio-venous fistulas commonly occur other than by progression of natural disease, for example, as a result of accidents and gun-shot wounds. Each of these diseases has lead to the development of specialized treatments ranging from minimally-invasive techniques to more conventional open surgical techniques.

For example, a health problem afflicting an older segment of the population is the occurrence of disease that weakens the arteries and other body vessels, developing into aneurysms that may rupture, often with fatal consequences. A conventional treatment of aneurysms, especially those occurring in the abdominal aorta, has involved invasive surgery to resect and remove the diseased body vessel and replace it with either a native vessel, harvested from elsewhere in the body, or a synthetic graft material. Such treatments typically pose a major risk to the patient's health, and frequently cannot be undertaken at all, if (as is common) the patient is in poor health.

A number of vascular prostheses have therefore been developed that permit a synthetic graft to be placed transluminally within the aneurysm, to isolate the aneurysm from fluids flowing in the body vessel and which relieve pressure from the aneurysm. These previously known vascular prostheses generally anchor a tubular synthetic graft inside the body vessel, on either end of the aneurysm, using a stent, as described, for example, in U.S. Pat. No. 5,078,726 to Kreamer and U.S. Pat. No. 5,219,355 to Parodi et al.

Similarly, U.S. Pat. No. 5,456,713 to Chuter and U.S. Pat. No. 5,275,622 to Lazarus describe stent-graft combinations, delivered transluminally, comprising a tubular graft having barbed self-expanding anchors secured by sutures to the ends of the tubular graft. U.S. Pat. No. 5,366,473 to Winston et al. describes a stent graft combination wherein a tubular graft has a self-expanding coiled sheet stent riveted to either end of the graft.

A drawback of the foregoing stent-graft systems is that they generally require a large access site (e.g., 16–22 Fr), which limits the applicability of such devices to larger vessels. Specifically, the graft material generally must be bunched or gathered to fit within the delivery system, as described in the above-mentioned Chuter, Winston et al. and Lazarus patents, but cannot be compacted within the delivery system, or problems may arise relating to unfurling of the graft during deployment. In addition, clinical testing of previously-known stent-graft combinations has revealed problems with inadequate sealing between the graft material and the anchors, and where the graft contacts the body lumen proximally and distally of the aneurysm.

Other arrangements for isolating aneurysms are also known. U.S. Pat. No. 4,577,631 to Kreamer describes a method of gluing a graft across an aneurysm using a biocompatible adhesive. U.S. Pat. No. 5,211,658 to Clouse describes a stent-graft combination wherein a temperature activated skeleton is first deployed in a body lumen so that it spans an aneurysm; a graft then is affixed to the deployed skeleton. U.S. Pat. No. 5,405,379 to Lane describes a polypropylene sheet which is rolled into a coil, and permitted to self-expand within the body lumen so that it spans the aneurysm. U.S. Pat. No. 5,100,429 to Sinofsky et al. describes a coiled sheet stent including a layer of collagen-based material which is heated by an energy source so that it fuses to form a rigid structure.

Each of the foregoing arrangements has inherent disadvantages peculiar to their designs that makes the use of such designs impractical. These disadvantages range from the mechanical complexity of the Kreamer, Clouse and Sinofsky et al. designs, to the inability to obtain an adequate seal at ends of the Lane device.

With respect to treatment of obstructive vascular disease, a number of prostheses have been developed for intraluminal deployment. These devices, of which the Palmaz-Schatz stent sold by Cordis Corporation, Miami Lakes, Fla., is typical, treat obstructive disease, for example, in the coronary arteries, by retaining the patency of vessel following an angioplasty procedure. Most previously known prostheses designed to treat obstructive disease include a plurality of throughwall openings to promote cellular proliferation. A drawback of such designs, however, is that the openings may also promote reformation of the obstruction over time.

Previously known techniques for treating arterio-venous fistulas, which permit oxygenated blood to be shunted from an artery directly to the venous system, typically involve open surgery. Thus, for example, a gun-shot victim, given the present state of the art, must undergo surgery to repair an arterio-venous fistula. The present state-of-the art lacks any devices which may be readily deployed, even on an interim basis, to prevent excessive blood loss while awaiting surgery.

In view of the foregoing, it would be desirable to provide a prosthesis for treating aneurysms, obstructive disease of vessels and body organs, and arterio-venous fistulas, that is simple in design and easily deployed.

It would further be desirable to provide a prosthesis for treating aneurysms, obstructive disease of vessels and body organs, and arterio-venous fistulas, that overcomes problems associated with the bulkiness of prior art stent-graft systems, and that can be readily scaled for use in a variety of vessels, thereby enabling treatment of disease in even very small body lumens.

It would further be desirable to provide a prosthesis for treating aneurysms, obstructive disease of vessels and body organs, and arterio-venous fistulas, that provides an internal bandage, for example, that can stem blood loss through an arterio-venous fistula, or provide a positive seal at the ends of a graft to reduce bypass flow.

SUMMARY OF THE INVENTION

In view of the foregoing, it is an object of the present invention to provide a prosthesis for treating aneurysms, obstructive disease of vessels and body organs, and arterio-venous fistulas, that is simple in design and easily deployed.

It is another object of this invention to provide a prosthesis for treating aneurysms, obstructive disease of vessels and body organs, and arterio-venous fistulas, that overcomes problems associated with the bulkiness of prior art stent-graft systems, and that can be readily scaled for use in a variety of vessels, thereby enabling treatment of disease in even very small body lumens.

It is a further object of the invention to provide a prosthesis for treating aneurysms, obstructive disease of vessels and body organs, and arterio-venous fistulas, that provides an internal bandage, for example, that can stem blood loss through an arterio-venous fistula, or provide a positive seal at the ends of a graft to reduce bypass flow.

These and other objects of the invention are accomplished by providing a prosthesis comprising a coiled sheet portion having biocompatible graft material affixed thereto, so that the graft material is wound within the coiled sheet portion when it is reduced to its delivery state. The graft material, preferably a polytetrafluoroethylene ("PTFE") or polyester material, is affixed to the coiled sheet portion using, for example, a biocompatible adhesive, sintering or suturing, and serves to alter flow to a portion of a body lumen in which the prosthesis is deployed. The graft may be affixed to an interior or exterior surface of the coiled sheet portion, or may comprise alternating layers of graft and coiled sheet portions (i.e., a graft affixed between inner and outer coiled sheet portions or a coiled sheet portion with graft material disposed on either side).

In a preferred embodiment, the coiled sheet portion of the prosthesis comprises a mesh formed from a shape-memory alloy, such as a nickel-titanium alloy, that exhibits superelastic behavior at body temperature. The coiled sheet preferably includes one or more rows of locking teeth along a longitudinal edge that interengage the mesh to retain the prosthesis at a desired expanded diameter. In addition, the mesh may include a plurality of radially outwardly directed projections along one or both ends that engage an interior surface of a body lumen.

The mesh of the coiled sheet may have a size suitable for use in smaller body arteries, such as the coronary arteries and carotid arteries, or may be scaled to accommodate larger vessels such as the abdominal aorta and iliac arteries. For larger vessels, the mesh of the coiled sheet may include articulations to assist in maneuvering the prosthesis through tortuous body passageways.

The graft material used in the prosthesis of the present invention may be either fluid impermeable, for example, for treating arterio-venous fistulas or semi-permeable, for example, to permit nourishment of vessel intima when treating occlusive vascular disease while reducing throughwall cell proliferation. The graft material may also be impregnated with one or more drugs to achieve to provide a desired effect. The graft material may also serve to reduce embolization of frangible material from the interior of body lumen following, for example, an angioplasty procedure.

In addition to the foregoing applications, a pair of prostheses constructed in accordance with the present invention may be advantageously employed, one at either end, for positively sealing the ends of a conventional tubular graft.

Methods of making and deploying the prosthesis of the present invention are also provided. In accordance with these methods, the prosthesis is first deployed in a body lumen from a reduced delivery state. A dilation element is then disposed within the prosthesis and expanded, thereby locking the prosthesis at an expanded diameter and positively sealing the graft material against the interior surface of the body lumen.

BRIEF DESCRIPTION OF THE DRAWINGS

Further features of the invention, its nature and various advantages will be more apparent from the accompanying drawings and the following detailed description of the preferred embodiments, in which.

DETAILED DESCRIPTION OF THE PREFERRED EMBODIMENTS

The present invention provides prostheses for treating aneurysms, obstructive disease of vessels and body organs, and arterio-venous fistulas, that overcome the limitations of previously known minimally-invasive treatment systems. In particular, a prosthesis constructed in accordance with the present invention provides altered fluid flow through a section of body lumen with a device that is simple, yet elegant in design, easy to deploy, is readily scalable for use throughout the body, and provides the functionality of an internal bandage.

Figure 1:
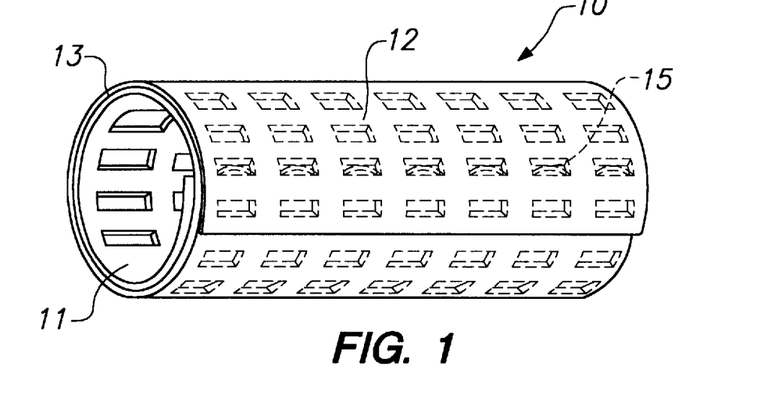
FIG. 1 is a perspective view of an illustrative prosthesis constructed in accordance present invention.

Referring to FIG. 1, illustrative prosthesis 10 constructed in accordance the present invention is described. Because prosthesis 10 includes certain features of both conventional coiled sheet stents, as described, for example, in U.S. Pat. No. 5,443,500 to Sigwart, incorporated herein by reference, and conventional synthetic tubular grafts, it is referred to hereinafter as a "graft stent."

Graft stent 10 comprises coiled sheet portion 11 including a resilient lattice or mesh onto which a layer of biocompatible graft material 12 has been affixed. Graft material 12 may have a permeability selected to address a particular application, and may be impregnated with one or more drugs to effect a desired treatment. Thus, for example, graft material 12 may be fluid impervious for the treatment of arterio-venous fistulas, but may be semi-permeable where it is desired to permit nutrients to pass through the graft material, yet prevent cell proliferation therethrough. In yet other applications, the graft material may include a porosity sufficient to maintain a pressure differential between fluids disposed on either side.

Graft stent 10 preferably comprises a biocompatible material, such as a shape-memory alloy (e.g., nickel-titanium), while biocompatible graft material preferably comprises a PTFE or polyesther fabric. Graft material 12 is affixed to coiled sheet portion 11 by any of the methods described hereinbelow, including a biocompatible adhesive 13, by sintering, sutures, or combination of thereof, so that the graft material is wound within the turns of the coiled sheet portion in the reduced diameter delivery state. Graft stent 10 may include a single coiled sheet portion sandwiched between multiple layers of graft material, or a single layer of graft material sandwiched between multiple coiled sheet portions.

Figure 2:
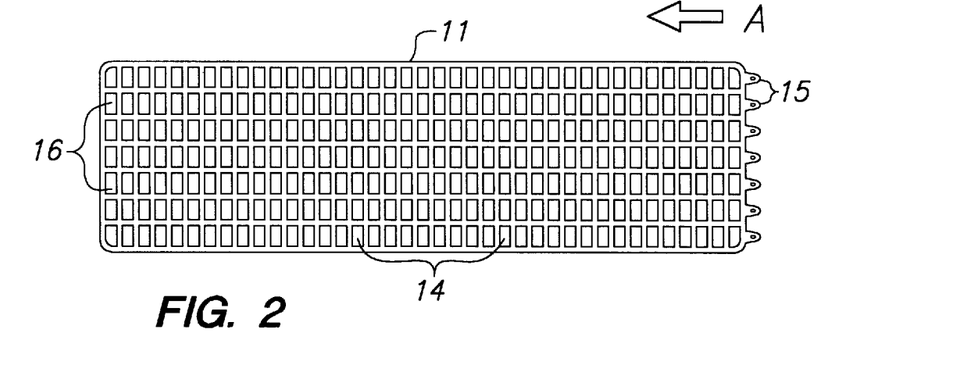
FIG. 2 is a plan view of a flat strip having a rectangular lattice suitable for forming the coiled stent portion of the prosthesis of the invention.

Referring to FIG. 2, coiled sheet portion 11 of graft stent 10 comprises a thin flat sheet of material, about 1.0 to 5.0 mils thick, which is formed into a lattice having a multiplicity of openings 14, for example, by die and punch, laser cutting or chemical etching. Openings 14 reduce the overall mass of the graft stent, provide some longitudinal flexibility when the graft stent is contracted, and may be used to enhance fixation of the graft material to the coiled sheet portion, as described hereinbelow. Openings 14 may be triangular-shaped, diamond-shaped, rectangular-shaped or circular-shaped, or any combination thereof, and are preferably arranged in a lattice that provides about 50% open space or more.

In accordance with the present invention, coiled sheet portion 11 of graft stent 10 preferably includes one or more rows of teeth 15 adjacent to one edge that mate with openings 16 on an opposing overlapping edge of the coiled sheet. Teeth 15 serve to lock the graft stent at a selected expanded diameter, as described in the incorporated Sigwart patent and in U.S. Pat. No. 5,007,926 to Derbyshire, also incorporated herein by reference. This locking action provides a tight seal of the graft material against the interior surface of the body lumen. When used to treat obstructive vascular disease, the tight seal serves to retain patency of the vessel and reduce the potential for embolization; for arterio-venous fistulas, the seal reduces shunted flow; for aneurysms, the seal reduces the risk of bypass flow around the edges of the graft stent. In a preferred embodiment, teeth 15 are sufficiently long to engage mating openings 16 so as to stretch any graft material covering openings 16, but without perforating that graft material.

Alternatively, graft stent 10 may be secured in place in the body lumen using a coiled sheet portion that retains several overlapping turns even in the expanded state, as described, for example, in U.S. Pat. No. 5,306,294 to Winston et al.

Coiled sheet portion 11 may be formed from any biocompatible material, such as a thermal shape-memory polymer or metal, super-elastic material such as a nickel-titanium alloy, or other biocompatible resilient material such as a stainless steel, tantalum, platinum or tungsten alloy. In a preferred embodiment, a nickel-titanium alloy is used that has an austenite transition temperature slightly below body temperature, so that the coiled sheet portion exhibits super-elastic behavior when deployed. Also in the preferred embodiment, the nickel-titanium coiled sheet portion is heat treated, using processes known in the art, for activating the shape-memory effect of the material so that the coiled sheet portion has an expanded diameter in the austenite phase.

Coiled sheet portion 11 of graft stent 10 may be formed in a variety of sizes depending upon the intended application. For example, a graft stent for use in the treatment of aneurysms of the abdominal aorta may require a length of 8–12 cm and an expanded diameter of 2–4 cm, while a graft stent for use in a main branch artery, or the iliac arteries, may require a length of 2–8 cm and an expanded diameter of 8–12 mm. Of course, graft stents for use in other vessels, for example, to treat A-V fistulas or obstructive disease, may be smaller. While graft stents for use in vessels under about 2.0 cm may employ a single coiled sheet portion 11 of FIG. 2 (as shown in FIG. 1), in accordance with the present invention, multiple coiled sheet portions also may be used to built longer graft stents. In addition, as described hereinafter, the graft stent of the present invention may be advantageously used to anchor a conventional tubular graft in place across a large aneurysm.

Referring now to FIGS. 3, and 4A–4F the process of making a graft stent in accordance with the present invention is described. For illustrative purposes, the graft stent comprises three coiled sheet portions 21 (similar to that of FIG. 2), thereby providing a graft stent with an overall length about three times that of graft stent 10 of FIG. 1. Coiled sheet portions 21 are disposed on sheet 20 of a biocompatible of graft material, such as PTFE or polyesther fabric, which is cut to accommodate the coiled sheet stent portions lying side-by-side. The coiled sheet portions 21 are then fastened to the sheet of graft material using one of the methods described hereinbelow. Any excess portion of the sheet 20 may then be trimmed away, for example, with a razor knife to form the completed graft stent. The graft stent is then sterilized, for example, using a conventional ethylene oxide process.

Figure 3:
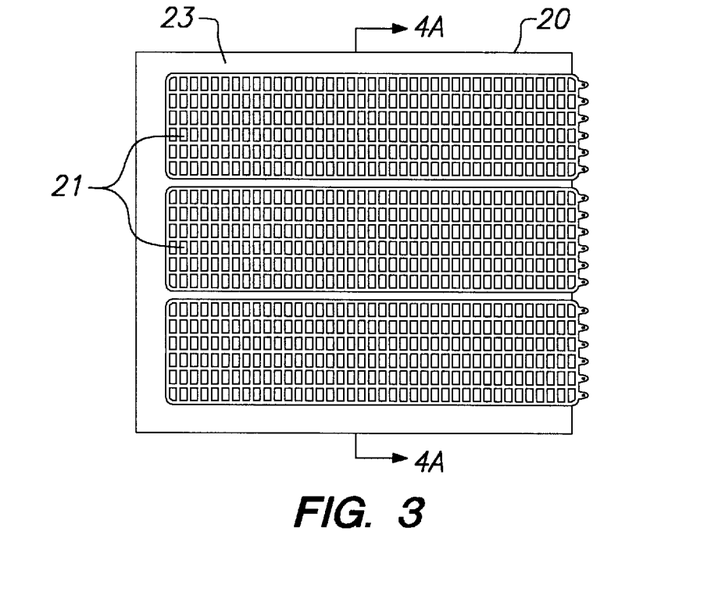
FIG. 3 is plan view of a prosthesis constructed in accordance with the present invention during a step of manufacturing the prosthesis.
Figure 4A:
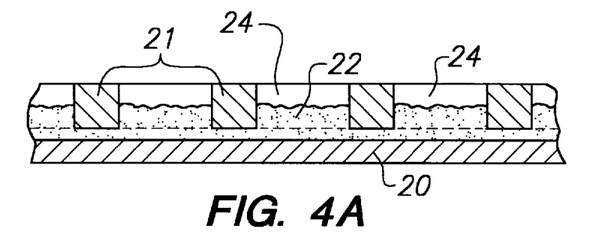
FIGS. 4A–4C, 4D and 4E–4F are, respectively, alternative cross-sectional views, a plan view, and exploded perspective views of the prosthesis of FIG. 1 constructed in accordance with various methods of the present invention.

In a first method of constructing a graft stent in accordance with the invention, illustrated in FIG. 4A, coiled sheet portions 21 are coated with a thin layer of a biocompatible adhesive 22 (for example, with a brush or by dipping), such as a liquid polyurethane resin or epoxy, that remains flexible when dry. While the adhesive is still wet, the coiled sheet portions 21 are positioned side-by-side on sheet 20 as shown in FIG. 3. When adhesive 22 dries, it bonds coiled sheet portions 21 to sheet 20, and provides a joint between the neighboring coiled sheet portions 21. Excess portions 23 of sheet 20 (for example, around the edges of coiled sheet portions 21) may then be trimmed to complete assembly of the graft stent.

When finished, a graft stent constructed by the above-described process has a cross-section similar to that depicted in FIG. 4A, in which adhesive 22 forms a layer, preferably about 0.1 mil thick, that bonds graft material 20 to the outer surface of coiled sheet portion 21. Adhesive 22 also extends slightly into the open spaces 24 formed by multiplicity of openings 14 and between edges of the adjacent coiled sheet portions 21. Applicant has observed that a layer of polyurethane adhesive, employed as described above with respect to FIGS. 3 and 4A, provides good column strength in a graft stent built from a plurality of separate coiled sheet portions. Accordingly, the graft stent of the present invention may be built up to any desired length using the components and processes described hereinabove.

Figure 4B:
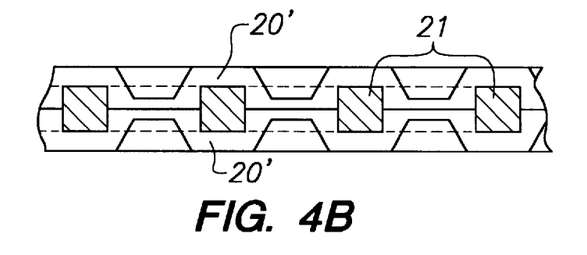

Referring to FIG. 4B, a method of making a graft stent by an alternative method of sintering the graft material to the coiled sheet portion is illustrated. In this embodiment, the coiled sheet portion is sandwiched between two layers of a biocompatible graft material 20', such as PTFE. The assembly is then heated to raise the graft material to a temperature at which the two layers contact one another through the multiplicity of openings 14, and fuse or sinter together, thereby forming a waffle shape. Pressure may be applied to the assembly during the heating process to accelerate the fusing or sintering step. In addition, a thin layer of biocompatible adhesive may be employed to retain the assembly together prior to the heat treatment. Consequently, the two layers of graft material 20' disposed on the opposite sides of coiled sheet portion 21 form a single fused layer within which coiled sheet portion 21 is embedded.

Figure 4C:
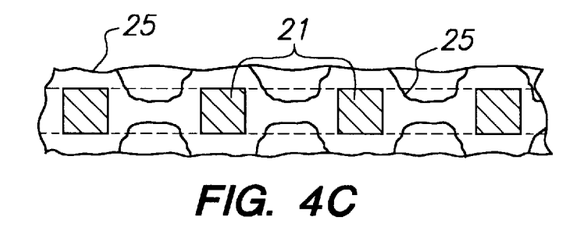

In FIG. 4C another method of making a stent in accordance with the present invention is described. In this method, the coiled sheet portion is dipped into a liquid polymer, such as urethane. The coiled sheet portion is then withdrawn from the liquid polymer so that the liquid forms a film 25 extending across the multiplicity of openings 14 in the coiled sheet portion 21. The coiled sheet portion may then be disposed on a section of graft material, as in the first method described above, so that the coated stent portion adheres to the graft material. Alternatively, the liquid polymer film 25 may be permitted to air dry without being bonded to a graft portion. In this latter embodiment, the polymer film itself serves as the graft material.

Figure 4D:
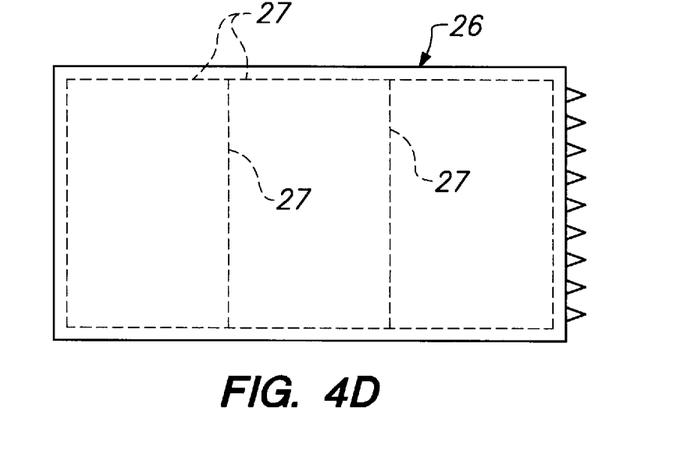

With respect to FIG. 4D, yet another method of making a graft stent in accordance with the present invention is described. In the embodiment of FIG. 4D, graft stent 26 if formed by sewing or suturing coiled sheet portions 21 to graft material 20, with stitches or sutures 26 extending through some of the multiplicity of openings of the coiled sheet portion. In a preferred method, the coiled sheet portions are first dipped in a biocompatible adhesive and adhered to the graft material to retain the graft material in a desired relation to the coiled sheet portion. Biocompatible stitches or sutures 27 are then applied by machine or by hand along the edges and at intervals along the graft material to affix the graft material to the coiled sheet portion.

Figure 4E:
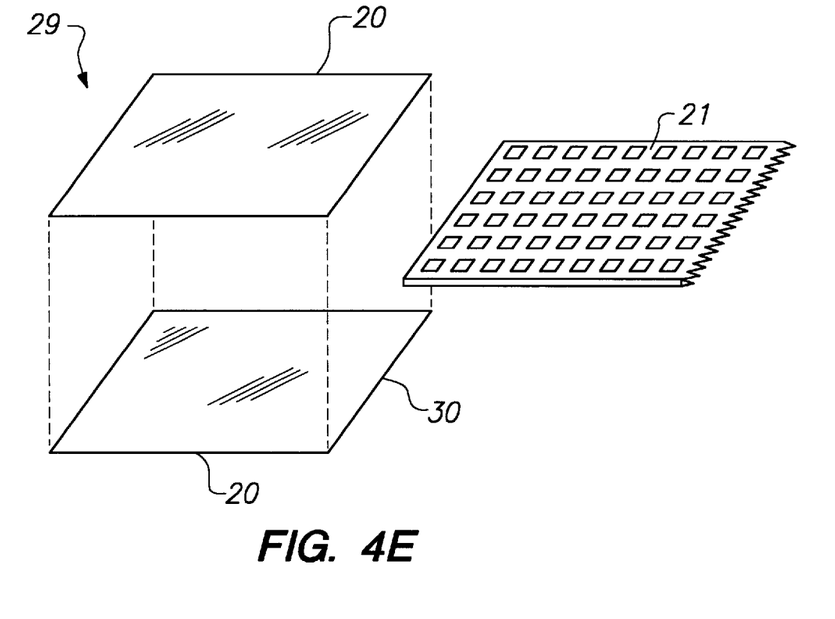

In FIG. 4E, graft stent 28 is formed by first sewing two pieces of graft material 20 together along three sides to form "pillow case" structure 29. Coiled sheet portion 20 is then inserted within structure 29, so that the edge carrying the locking teeth projects from open edge 30. The graft material is then affixed to coiled sheet portion 20 with single machine- or hand-stitched seam 31. The embodiment of FIG. 4D enables the graft material to experience some lateral movement with respect to the coiled sheet portion, which may be desirable in certain circumstances.

Figure 4F:
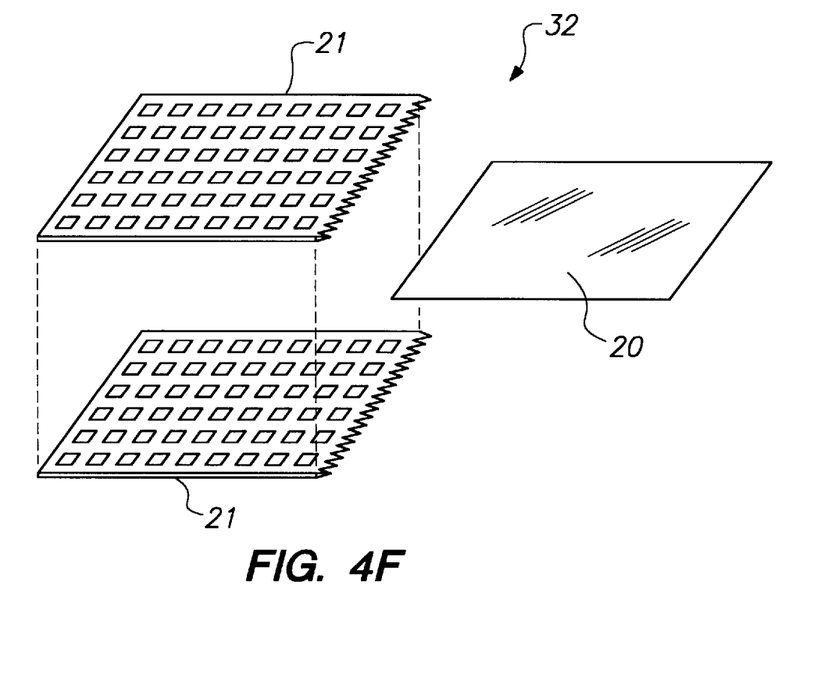

In FIG. 4F, a yet further alternative embodiment is the graft stent of the present invention is described. Graft stent 32 comprises a single sheet of graft material 20 sandwiched between two coiled sheet portions 21. Coiled sheet portions 21 may be glued together by a suitable biocompatible adhesive, or stitched or sutured to one another, thereby trapping the graft material in between the coiled sheer portions. Alternatively, one of the coiled sheet portions may include projections, while the other includes mating sockets to accept the projections, thereby retaining the assembly together. The embodiment of FIG. 4F of the invention is particularly well-suited for addressing problems relating to in-situ swelling of graft material in prior art grafts, because swelling of the graft material is limited by the coiled sheet portions.

Advantageously, with respect to the above-described embodiments of the present invention, because the lattice of the coiled sheet portion does not undergo longitudinal or radial distortion during deployment, the graft material of the graft stent of the present invention is not subjected to stress or distortion that could lead to perforation of the graft material during deployment and use.

In addition, as a further step of the manufacture of any of the above embodiments of the graft stent of the present invention, the graft material may be impregnated with one or more drugs to achieve a desired treatment goal. For example, the outer surface of the graft stent may coated with an anti-heparin drug, such as Proamine, to enhance clotting of blood captured outside the graft stent (for example, to promote thrombosis within an aneurysm or to prevent embolization of frangible material from the vessel wall), and may include a coating of a heparin-type compound on the inner surface of the graft stent to reduce the risk of thrombosis within the vessel.

Figure 5A:
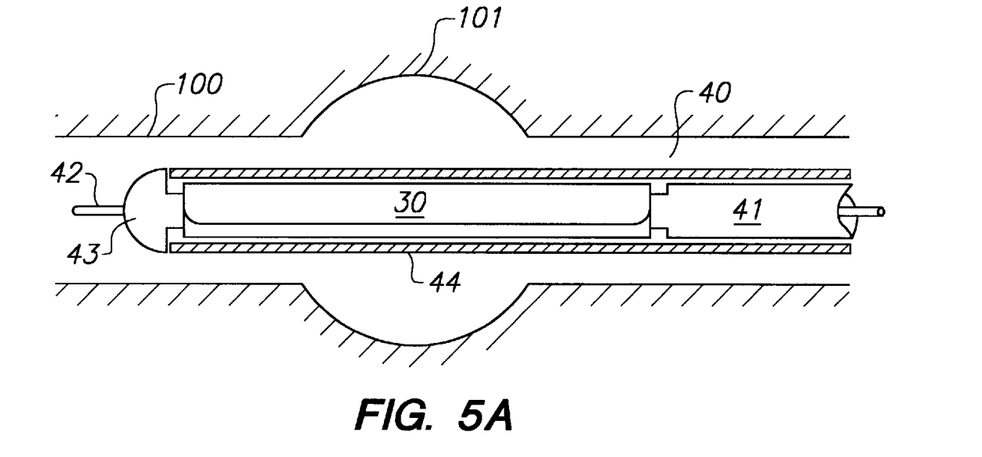
FIGS. 5A–5C are views showing the steps of deploying a prosthesis constructed in accordance with the present invention to span an idealized aneurysm.
Figure 5B:
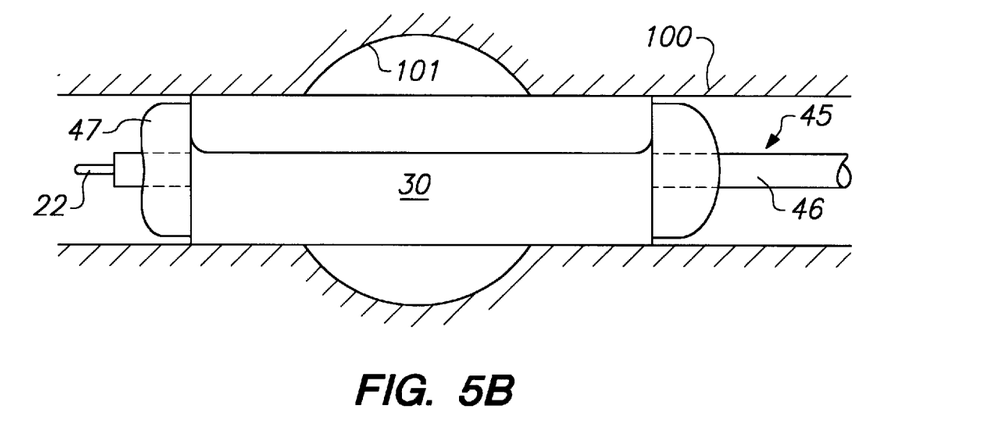
Figure 5C:
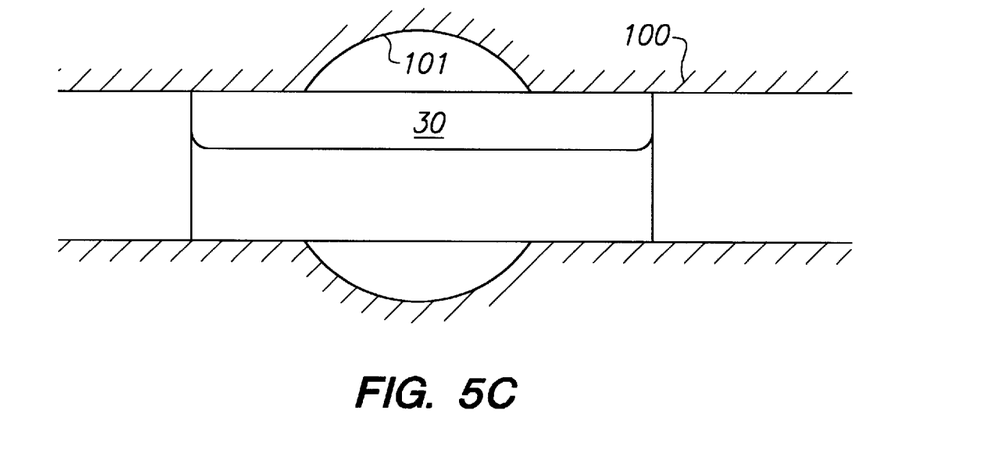

Referring now to FIGS. 5A–5C, the steps of deploying the graft stent of the present invention to treat an idealized aneurysm are described. It will be understood, however, that the steps of deploying a graft stent to treat an A-V fistula or obstructive disease of a vessel or body-organ apply equally.

Graft stent 30 is formed using the components and the methods of manufacture described hereinabove. The graft stent is then rolled about a mandrel in a direction indicated by arrow A in FIG. 2 (so that teeth 15 are inside the coil) to a reduced diameter for delivery. As of course will be understood by one skilled in the art, graft stent is contracted to the reduced diameter by winding the coiled sheet portion to form a series of overlapping turns. The contracted graft stent is then loaded into a sheath for delivery, as described, for example, in Sigwart U.S. Pat. No. 5,443,500 or Garza et al. U.S. Pat. No. 4,665,918, the entireties of which are incorporated herein by reference, which retains the graft stent in its contracted diameter.

In FIG. 5A, graft stent 30 is shown rolled to its contracted state and disposed within delivery system 40, such as described in the above-incorporated Garza et al. patent. For clarity, the detail of the lattice of graft stent 30 is omitted in FIGS. 5A–5C. Delivery system 40 includes catheter 41 having a central lumen for accepting guide wire 42, nose cone 43 and outer sheath 44. Delivery system 40 is inserted into body lumen 100 to be treated, for example, having aneurysm 101, through a major vessel along guide wire 42, as is well-known in the art, until the mid-point of the graft stent is located within aneurysm 101.

Once the location of delivery system 40 is established, for example, using fluoroscopy and standard angiographic techniques, outer sheath 44 of the delivery system is retracted to release graft stent 30 into body lumen 100 so that it spans aneurysm 101. When released from outer sheath 44, graft stent 30 unwinds at least partially to conform to the diameter of the body lumen.

With respect to FIG. 5B, mechanical expander 45, which may be a balloon catheter 46 carrying compliant balloon 47, is transluminally inserted within graft stent 30 and expanded. As balloon 47 expands, graft stent 30, the teeth on the inner edge ratchet across the openings in the opposing edge of the graft stent, so that the graft is locked at progressively larger diameters (as seen in FIG. 1). Balloon 47 may be inflated, for example, while visualized with conventional fluoroscopic and angiographic techniques, until graft stent 30 is expanded to a diameter at which the teeth of the coiled sheet portion positively lock the graft stent against the healthy portions of body lumen 100 and prevent bypass flow through aneurysm 101.

Once graft stent 30 has been locked into position within body lumen 100, balloon 47 is contracted, and balloon catheter 46 is withdrawn from the body lumen. Because the teeth interengage with the openings on the opposing overlapping edge of the graft stent, graft stent 30 retains the expanded diameter attained during the step of the balloon expansion, as illustrated in FIG. 5C, and does recoil elastically to the shape assumed when initially released from outer sheath 44.

Importantly, because graft stent 30 is elastically expanded by unwinding from its rolled position, no stress is applied to the graft material, thereby reducing the risk of perforation. Moreover, since the graft stent of the present invention preferably comprises a coiled sheet portion formed from a super-elastic shape memory alloy, such as a nickel-titanium alloy, the graft stent may be conformed to a wide range of body lumen diameters while providing adequate radial strength.

As also will be apparent to one of skill in the art, the graft stent of the present invention is distinguished from other previously known stent graft combinations in that while the graft material covers the stent, no bunching or gathering of the graft material occurs when the graft stent is contracted to its delivery diameter. Instead, the graft material is wound along with the coiled sheet portion of the graft stent to a contracted diameter for delivery, and features a longitudinal seam that is closed only when the graft stent is fully deployed. Accordingly, the graft stent of the present invention may be contracted to extremely small diameters, enabling the use of grafts in vessels not accessible using previously known stent graft delivery systems.

Figure 6:
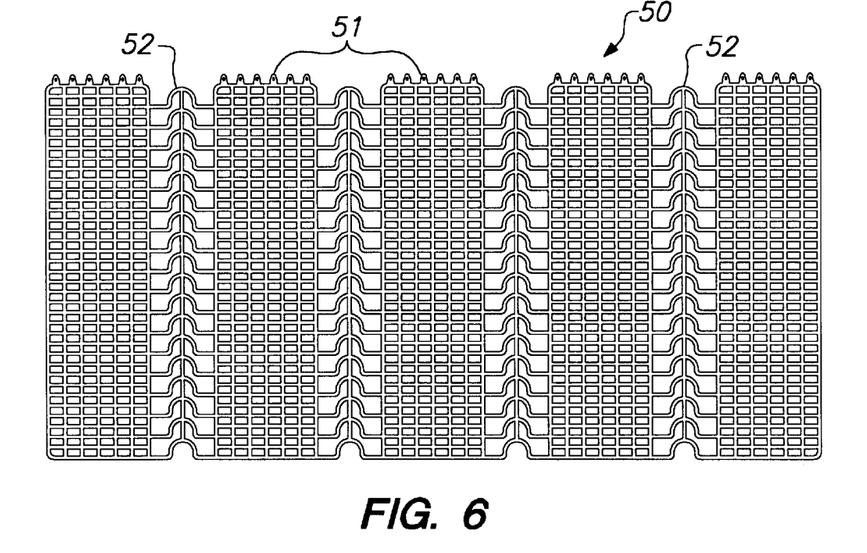
FIGS. 6 and 7 are plan views of alternative articulated mesh designs suitable for use with the prosthesis of the present invention.
Figure 7:
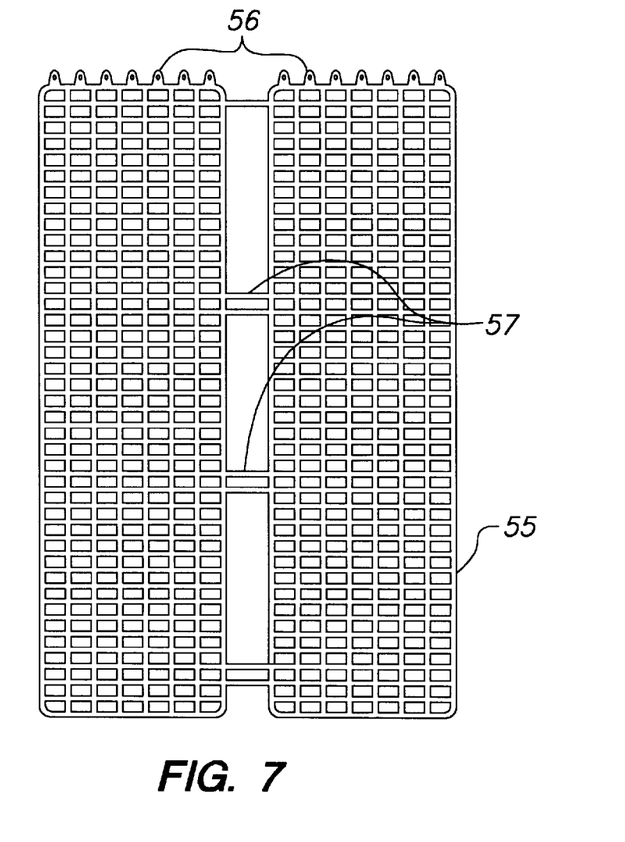

Referring now to FIGS. 6 and 7, alternative embodiments of the coiled sheet portion of the inventive graft stent are described. Coiled sheet portion 50 of FIG. 6 comprises a plurality of elements 51 joined by serpentine articulations 52, while coiled sheet portion 55 of FIG. 7 comprises a plurality of elements 56 joined by linear articulations 57. Coiled sheet portions 51 and 56 illustratively employ the lattice design of coiled sheet portion 11 of FIG. 2. Articulations 52 and 57 are contemplated to give coiled sheet portions 50 and 55, respectively, greater flexibility for passing through tortuous body lumens. This feature may be especially useful where the overall graft stent length may exceed the column strength achievable using individual coiled sheet elements, as described above with respect to FIG. 3.

Figure 8A:
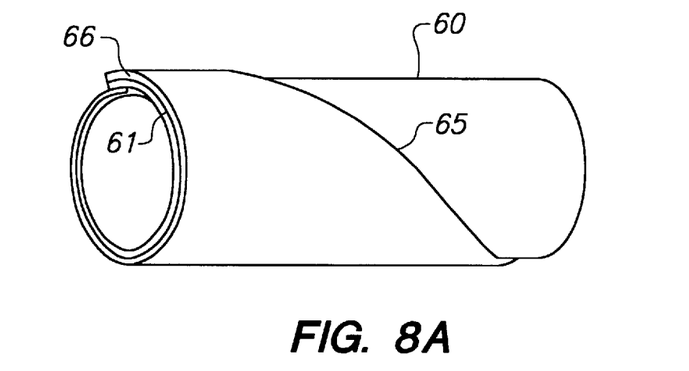
FIGS. 8A and 8B are perspective and plan views, respectively, of a prosthesis employing a coiled sheet mesh designed for large vessels, in which the detail of FIG. 8B has been omitted from FIG. 8A for clarity.
Figure 8B:
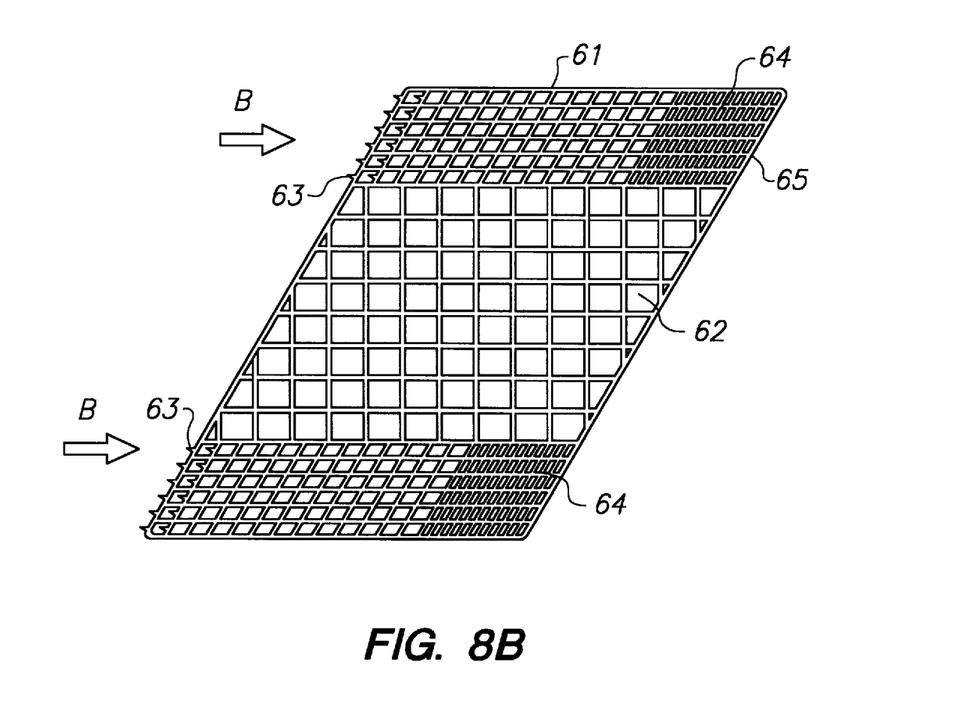

FIGS. 8A and 8B provide a further alternative for creating graft stent 60 for use in larger vessels. FIG. 8B depicts coiled sheet portion 61 having a variable geometry of openings 62 in the mesh lattice. The mesh shown is expected to provide greater flexibility for a large graft stent, for example, having a length about 10 cm and a diameter of 2–4 cm. Coiled sheet portion 61 includes teeth 63 that mate with openings 64 in opposing overlapping edge 65 of coiled sheet portion 61.

Coiled sheet portion 61 has suitable graft material 66 affixed to its outer surface, using the methods of manufacture described hereinabove. When rolled in the direction indicated by arrows B in FIG. 8B, graft stent 60 forms the tubular member shown in FIG. 8A (detailed omitted), wherein overlapping edge 65 of the graft stent spirals around the outer surface of the prosthesis. Graft stent 60 of FIGS. 8A and 8B is deployed in a manner similar to that described above with respect to FIGS. 5A to 5C. It is contemplated that the spiral nature of the overlapping edge will advantageously distribute radial expansive forces around the circumference of the graft stent, thus reducing the risk of buckling.

Figure 9A:
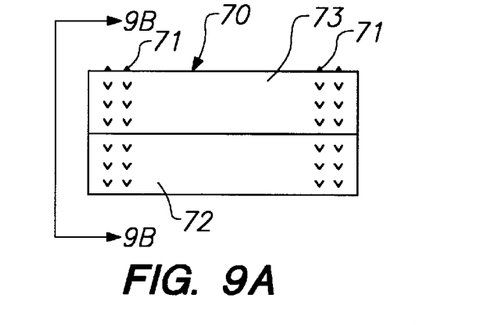
FIGS. 9A and 9B are front and side elevation views, respectively, of a prosthesis constructed in accordance with the present invention that includes radially outwardly projecting barbs from its surface near both ends.
Figure 9B:
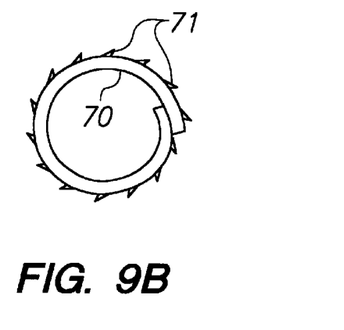

Referring now to FIGS. 9A and 9B, an further alternative embodiment of the present invention is described with respect to graft stent 70. Graft stent 70 preferably is constructed as described above with respect to the graft stent 10 of FIG. 1, except that graft stent 70 includes rows of radially projecting barbs 71 on its outer surface in regions 72 and 73 adjacent the ends of the graft stent. Barbs 71 are oriented so that they freely permit expansion of the coiled sheet portion, but engage the interior of the body lumen to resist contraction of the stent due to external radial compressive force. Barbs 71 of graft stent 70 preferably are formed as part of the etching or punching process during formation of the coiled sheet stent portion of the graft stent. During assembly of graft stent 70, using any of the methods described hereinabove, barbs 71 are permitted to pierce and protrude through the graft material.

Figure 10:
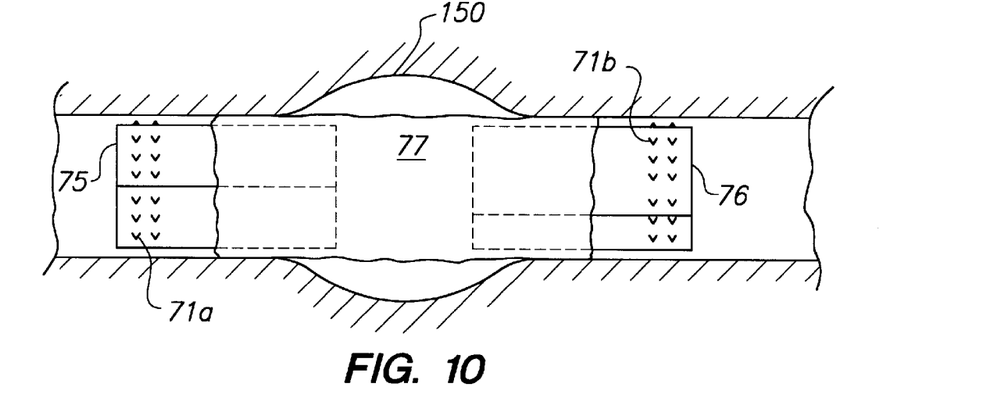
FIG. 10 is an front view of a variation of the prosthesis of FIG. 9 used to seal the ends of a conventional tubular graft to span an aneurysm.

In FIG. 10, a pair of graft stents 75, 76 are shown disposed in tubular graft 77 to seal the tubular graft to the healthy tissue proximal and distal of aneurysm 150. Tubular graft 77 may be a conventional fabric graft, constructed, for example, from a polyesther material. Graft stents 75 and 76 are "directional" in the sense that graft stent 75 preferably has barbs 71a disposed on its outer surface near its left hand end, whereas graft stent 76 has barbs 71 disposed on its outer surface near its right hand end. It is expected that graft stents 75 and 76 of the present invention will provide positive sealing at the proximal and distal ends of the tubular graft which has been unattainable heretofore.

Figure 11:
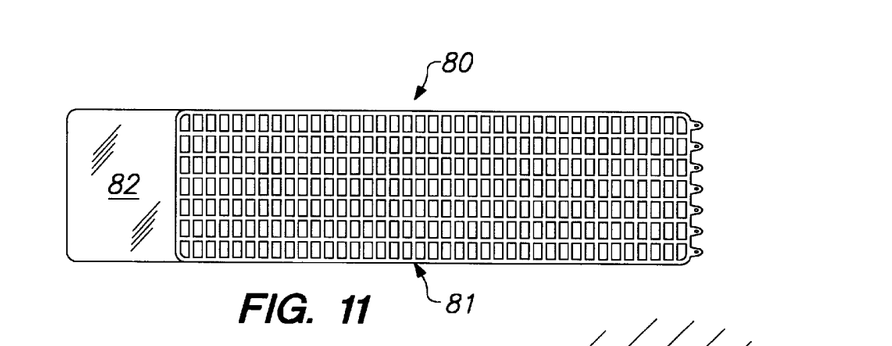
FIGS. 11 and 12 are plan and side views, respectively, of an alternative embodiment of the prosthesis of the present invention, in which graft material extends along an exterior edge of the prosthesis to form a flap that seals the longitudinal seam formed when the prosthesis is deployed and which assists in controlling the rate of deployment of the prosthesis.
Figure 12:
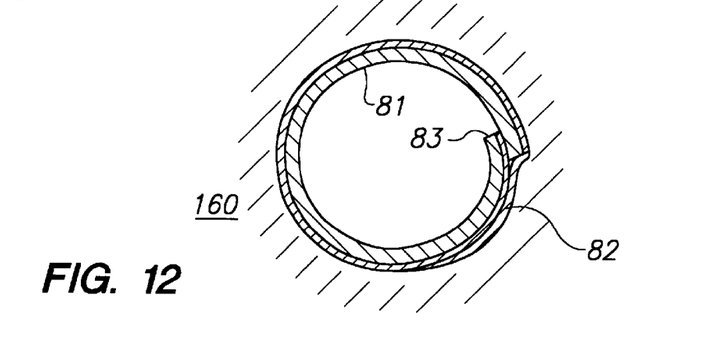

With respect to FIGS. 11 and 12, yet another alternative embodiment of graft stent 80 of the present invention is described. Graft stent 80 is similar in construction to the prosthesis of FIG. 1, except that during the manufacturing process, a length of graft material is left along the exterior edge of the coiled sheet portion 81 to form flap 82. As seen in FIG. 12, when graft stent 80 is deployed in body lumen 160, flap 82 overlaps longitudinal seam 83 in of the graft stent for an additional partial turn, for example, one-quarter to one-half the deployed circumference.

In accordance with the present invention, flap 82 of graft stent 80 performs three functions. First, the flap serves to seal longitudinal seam 83 to prevent leakage. Second, flap 82 serves to anchor the mid-section of the coiled sheet portion 81 to prevent bowing of the midsection of the coiled sheet when deployed. Third, the length of the flap may be adjusted to control the rate at which the coiled sheet portion expands when the graft stent is deployed. In particular, if flap 82 is selected to have a length of, for example, one-half of the deployed circumference, it is expected that flap 82 will provide a sliding resistance as the coiled sheet portion unwinds, thereby controlling the rate at which the coiled sheet is deployed.

As will be apparent to one of skill in the art based upon the foregoing disclosure, in an alternative embodiment of graft stent 80, the graft material may be affixed to the interior surface of the coiled sheet portion, rather than the external surface. In this case it may be desirable for the flap to extend from the inner edge of the coiled sheet portion (i.e., the edge with the locking teeth), so as to seal the longitudinal seam when deployed.

While preferred illustrative embodiments of the invention are described above, it will be apparent to one skilled in the art that various changes and modifications may be made therein without departing from the invention and it is intended in the appended claims to cover all such changes and modifications which fall within the true spirit and scope of the invention.

What is claimed is:

1. A prosthesis for treating a section of a body lumen, the prosthesis comprising:
   a coiled sheet portion having a contracted state wherein the coiled sheet portion is wound to a first diameter to form a series of overlapping turns, and an expanded state wherein the coiled sheet portion forms a tubular member having a second diameter greater than the first diameter, the coiled sheet portion expandable to the expanded state when released from the contracted state; and a graft material that is biocompatible affixed to the coiled sheet portion by a biocompatible adhesive, the graft material being wound within the overlapping turns of the coiled sheet portion when the coiled sheet portion is in the contracted state.

2. The prosthesis as defined in claim 1 wherein the coiled sheet portion further includes a plurality of teeth adjacent to an inner edge of the coiled sheet portion and a plurality of openings disposed on an opposing overlapping edge of the coiled sheet portion, the plurality of teeth interengaging the plurality of openings to lock the coiled sheet portion in the expanded state.

3. The prosthesis as defined in claim 2 wherein the coiled sheet portion further comprises a biocompatible material.

4. The prosthesis as defined in claim 1 wherein the graft material is also affixed to the coiled sheet portion by biocompatible sutures or stitches.

5. The prosthesis as defined in claim 1 wherein the graft material is affixed to an exterior surface of the coiled sheet portion.

6. The prosthesis as defined in claim 1 wherein the graft material is affixed to an interior surface of the coiled sheet portion.

7. The prosthesis as defined in claim 1 wherein the coiled sheet portion further includes a first end and a plurality of radially outwardly directed projections in a region disposed near a first end that engage an interior surface of the body lumen where the coiled sheet portion expands to the expanded state.

8. The prosthesis as defined in claim 1 wherein coiled sheet portion forms a tubular member having a longitudinal seam when the coiled sheet portion expands to the expanded state, the prosthesis further comprising a flap of graft material that extends from a longitudinal edge of the coiled sheet portion, the flap overlapping and sealing the longitudinal seam when the coiled sheet portion expands to the expanded state.

9. The prosthesis as defined in claim 1 wherein the coiled sheet portion further includes a portion defining a multiplicity of openings.

10. The prosthesis as defined in claim 9 wherein the multiplicity of openings includes openings of different sizes and orientations that improve the longitudinal flexibility of the coiled sheet portion.

11. The prosthesis as defined in claim 9 wherein the coiled sheet portion has an interior surface and an exterior surface, and the graft material is disposed on the interior surface, the prosthesis further comprising a layer of a biocompatible material disposed on the exterior surface.

12. The prosthesis as defined in claim 1 wherein the coiled sheet portion comprises first and second coiled sheet members, the graft material being interposed between the first and second coiled sheet portions.

13. The prosthesis as defined in claim 1 wherein the coiled sheet portion comprises a nickel-titanium alloy.

14. The prosthesis as defined in claim 1 wherein the graft material is polytetrafluoroethylene.

15. The prosthesis as defined in claim 1 wherein the biocompatible adhesive is a urethane compound.

16. The prosthesis as defined in claim 1 wherein the prosthesis has an overlapping edge and an exterior surface, the overlapping edge spiraling around the exterior surface in the expanded state.

17. The prosthesis as defined in claim 1 wherein the coiled sheet portion further includes a plurality of articulations that provide longitudinal flexibility of the prosthesis when transported through a tortuous body lumen.

18. The prosthesis as defined in claim 1 wherein the graft material is impregnated with at least one drug.

19. A prosthesis for treating a section of a body lumen, the prosthesis comprising:

a coiled sheet portion having a contracted state wherein the coiled sheet portion is wound to a first diameter to form a series of overlapping turns, and an expanded state wherein the coiled sheet portion forms a tubular member having a second diameter greater than the first diameter, the coiled sheet portion expandable to the expanded state when released from the contracted state; and a graft material that is biocompatible affixed to the coiled sheet portion by biocompatible sutures or stitches, the graft material being wound within the overlapping turns of the coiled sheet portion when the coiled sheet portion is in the contracted state.

20. The prosthesis as defined in claim 19 wherein the coiled sheet portion further includes a plurality of teeth adjacent to an inner edge of the coiled sheet portion and a plurality of openings disposed on an opposing overlapping edge of the coiled sheet portion, the plurality of teeth interengaging the plurality of openings to lock the coiled sheet portion in the expanded state.

21. The prosthesis as defined in claim 20 wherein the coiled sheet portion further comprises a biocompatible material.

22. The prosthesis as defined in claim 19 wherein the graft material is also affixed to the coiled sheet portion by a biocompatible adhesive.

23. The prosthesis as defined in claim 19 wherein the graft material is affixed to an exterior surface of the coiled sheet portion.

24. The prosthesis as defined in claim 19 wherein the graft material is affixed to an interior surface of the coiled sheet portion.

25. The prosthesis as defined in claim 19 wherein the coiled sheet portion includes a first end and a plurality of radially outwardly directed projections in a region disposed near a first end that engage an interior surface of the body lumen when the coiled sheet portion expands to the expanded state.

26. The prosthesis as defined in claim 19 wherein coiled sheet portion forms a tubular member having a longitudinal seam when the coiled sheet portion expands to the expanded state, the prosthesis further comprising a flap of graft material that extends from a longitudinal edge of the coiled sheet portion, the flap overlapping and sealing the longitudinal seam when the coiled sheet portion expands to the expanded state.

27. The prosthesis as defined in claim 19 wherein the coiled sheet portion further includes a portion defining a multiplicity of openings.

28. The prosthesis as defined in claim 27 wherein the multiplicity of openings includes openings of different sizes and orientations that improve the longitudinal flexibility of the coiled sheet portion.

29. The prosthesis as defined in claim 27 wherein the coiled sheet portion has an interior surface and an exterior surface, and the graft material is disposed on the interior surface, the prosthesis further comprising a layer of a biocompatible material disposed on the exterior surface.

30. The prosthesis as defined in claim 19 wherein the coiled sheet portion comprises first and second coiled sheet members, the graft material being interposed between the first and second coiled sheet portions.

31. The prosthesis as defined in claim 19 wherein the coiled sheet portion comprises a nickel-titanium alloy.

32. The prosthesis as defined in claim 19 wherein the graft material is polytetrafluoroethylene.

33. The prosthesis as defined in claim 19 wherein the biocompatible adhesive is a urethane compound.

34. The prosthesis as defined in claim 19 wherein the prosthesis has an overlapping edge and an exterior surface, the overlapping edge spiraling around the exterior surface in the expanded state.

35. The prosthesis as defined in claim 19 wherein the coiled sheet portion further includes a plurality of articulations that provide longitudinal flexibility of the prosthesis when transported through a tortuous body lumen.

36. The prosthesis as defined in claim 19 wherein the graft material is impregnated with at least one drug.

37. A prosthesis for treating a section of a body lumen, the prosthesis comprising:
a coiled sheet portion having a contracted state wherein the coiled sheet portion is wound to a first diameter to form a series of overlapping turns, and an expanded state wherein the coiled sheet portion forms a tubular member having a longitudinal seam and a second diameter greater than the first diameter, the coiled sheet portion expandable to the expanded state when released from the contracted state; and
a graft material that is biocompatible affixed to the coiled sheet portion, the graft material having a portion comprising a flap that extends beyond longitudinal edge of the coiled sheet portion, the graft material being wound within the overlapping turns of the coiled sheet portion when the coiled sheet portion is in the contracted state, the graft material forming a permanent substantially fluid-tight lumen when the coiled sheet portion expands to the expanded state, wherein the flap overlaps and seals the longitudinal seam.

38. The prosthesis as defined in claim 37 wherein the coiled sheet portion further includes a plurality of teeth adjacent to an inner edge of the coiled sheet portion and a plurality of openings disposed on an opposing overlapping edge of the coiled sheet portion, the plurality of teeth interengaging the plurality of openings to lock the coiled sheet portion in the expanded state.

39. The prosthesis as defined in claim 38 wherein the coiled sheet portion further comprises a biocompatible material.

40. The prosthesis as defined in claim 37 wherein the graft material is affixed to the coiled sheet portion by a biocompatible adhesive.

41. The prosthesis as defined in claim 37 wherein the graft material is affixed to the coiled sheet portion by sintering.

42. The prosthesis as defined in claim 37 wherein the graft material is affixed to the coiled sheet portion by biocompatible sutures or stitches.

43. The prosthesis as defined in claim 37 wherein the graft material is affixed to an exterior surface of the coiled sheet portion.

44. The prosthesis as defined in claim 37 wherein the graft material is affixed to an interior surface of the coiled sheet portion.

45. The prosthesis as defined in claim 37 wherein the coiled sheet portion includes a first end and a plurality of radially outwardly directed projections in a region disposed near a first end that engage an interior surface of the body lumen when the coiled sheet portion expands to the expanded state.

46. The prosthesis as defined in claim 37 wherein the coiled sheet portion further includes a portion defining a multiplicity of openings.

47. The prosthesis as defined in claim 46 wherein the multiplicity of openings includes openings of different sizes and orientations that improve the longitudinal flexibility of the coiled sheet portion.

48. The prosthesis as defined in claim 46 wherein the coiled sheet portion has an interior surface and an exterior surface, and the graft material is disposed on the interior surface, the prosthesis further comprising a layer of a biocompatible material disposed on the exterior surface.

49. The prosthesis as defined in claim 48 wherein the graft material is sintered so that the first layer is fused to the second layer through the multiplicity of openings.

50. The prosthesis as defined in claim 37 wherein the coiled sheet portion comprises first and second coiled sheet members, the graft material being interposed between the first and second coiled sheet portions.

51. The prosthesis as defined in claim 37 wherein the coiled sheet portion comprises a nickel-titanium alloy.

52. The prosthesis as defined in claim 37 wherein the graft material is polytetrafluoroethylene.

53. The prosthesis as defined in claim 40 wherein the biocompatible adhesive is a urethane compound.

54. The prosthesis as defined in claim 37 wherein the prosthesis has an overlapping edge and an exterior surface, the overlapping edge spiraling around the exterior surface in the expanded state.

55. The prosthesis as defined in claim 37 wherein the coiled sheet portion further includes a plurality of articulations that provide longitudinal flexibility of the prosthesis when transported through a tortuous body lumen.

56. The prosthesis as defined in claim 37 wherein the graft material is impregnated with at least one drug.

57. A prosthesis for treating a section of a body lumen, the prosthesis comprising:
a coiled sheet portion having an interior surface, an exterior surface, and a multiplicity of openings, the coiled sheet portion having a contracted state wherein the coiled sheet portion is wound to a first diameter to form a series of overlapping turns, and an expanded state wherein the coiled sheet portion forms a tubular member having a second diameter greater than the first diameter, the coiled sheet portion expandable to the expanded state when released from the contracted state; and
a graft material that is biocompatible, the graft material comprising a first layer disposed on the interior surface and a second layer disposed on the exterior surface, the first and second layers sintered together so that the first layer is fused to the second layer through the multiplicity of openings, the graft material being wound within the overlapping turns of the coiled sheet portion when the coiled sheet portion is in the contracted state, the graft material forming a permanent substantially fluid-tight lumen when the coiled sheet portion expands to the expanded state.

58. The prosthesis as defined in claim 57 wherein the coiled sheet portion further includes a plurality of teeth adjacent to an inner edge of the coiled sheet portion and a plurality of openings disposed on an opposing overlapping edge of the coiled sheet portion, the plurality of teeth interengaging the plurality of openings to lock the coiled sheet portion in the expanded state.

59. The prosthesis as defined in claim 57 wherein the coiled sheet portion further comprises a biocompatible material.

60. The prosthesis as defined in claim 57 wherein the coiled sheet portion includes a first end and a plurality of radially outwardly directed projections in a region disposed near a first end that engage an interior surface of the body lumen when the coiled sheet portion expands to the expanded state.

61. The prosthesis as defined in claim 57 wherein coiled sheet portion forms a tubular member having a longitudinal seam when the coiled sheet portion expands to the expanded state, the prosthesis further comprising a flap of graft material that extends beyond a longitudinal edge of the coiled sheet portion, the flap overlapping and sealing the longitudinal seam when the coiled sheet portion expands to the expanded state.

62. The prosthesis as defined in claim 57 wherein the multiplicity of openings includes openings of different sizes and orientations that improve the longitudinal flexibility of the coiled sheet portion.

63. The prosthesis as defined in claim 57 wherein the coiled sheet portion comprises a nickel-titanium alloy.

64. The prosthesis as defined in claim 57 wherein the graft material is polytetrafluoroethylene.

65. The prosthesis as defined in claim 57 wherein the prosthesis has an overlapping edge and an exterior surface, the overlapping edge spiraling around the exterior surface in the expanded state.

66. The prosthesis as defined in claim 57 wherein the coiled sheet portion further includes a plurality of articulations that provide longitudinal flexibility of the prosthesis when transported through a tortuous body lumen.

67. The prosthesis as defined in claim 57 wherein the graft material is impregnated with at least one drug.

\* \* \* \* \*